US012805705B2

(12) United States Patent
Zhao

(10) Patent No.: US 12,805,705 B2
(45) Date of Patent: Nov. 24, 2026

(54) ATTACHMENT OPTICS AND SYSTEM FOR FLUORESCENCE IMAGING IN OPEN SURGERY

(71) Applicant: OLYMPUS Winter & Ibe GmbH, Hamburg (DE)

(72) Inventor: Jianxin Zhao, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 476 days.

(21) Appl. No.: 18/389,058

(22) Filed: Nov. 13, 2023

(65) Prior Publication Data

US 2024/0268638 A1 Aug. 15, 2024

Related U.S. Application Data

(60) Provisional application No. 63/444,626, filed on Feb. 10, 2023.

(51) Int. Cl.
*A61B 1/00* (2006.01)
*H04N 23/55* (2023.01)
*H04N 23/56* (2023.01)

(52) U.S. Cl.
CPC ......... *A61B 1/00167* (2013.01); *H04N 23/55* (2023.01); *H04N 23/56* (2023.01)

(58) Field of Classification Search
CPC .... A61B 1/00167; H04N 23/56; H04N 23/55; G02B 21/0076; G02B 23/243
(Continued)

(56) References Cited

U.S. PATENT DOCUMENTS 5,568,312 A * 10/1996 Horton .................. G02B 13/18 359/434
10,054,772 B1 8/2018 Zobel
(Continued)

FOREIGN PATENT DOCUMENTS

CN 113960755 A * 1/2022 ......... G01N 21/6428
CN 115016110 A * 9/2022 ........... G02B 21/025
CN 115308177 A * 11/2022 ........... C12Q 1/6874

*Primary Examiner* — Stephone B Allen
*Assistant Examiner* — Boutsikaris Leonidas
(74) *Attorney, Agent, or Firm* — Scully, Scott, Murphy & Presser, P.C.

(57) ABSTRACT

Attachment optics for use with a camera head for fluorescence imaging in open surgery. The attachment optics including: an optical system comprising, in progression from distal to proximal: a distal group of first and second meniscus lenses, is the first meniscus lens having a negative meniscus and the second meniscus lens having a positive meniscus, a biplanar glass rod; and a third meniscus lens. Where the first and second meniscus lenses of the distal group are made from different glass types having Abbé numbers $\gamma_1$, $\gamma_2$ with $$|\gamma_1 - \gamma_2| < 20,$$

and refractive indexes $n_1$, $n_2$ with $$0.02 < |n_1 - n_2| < 0.07$$

and where the ratio of a focal length F of the optical system to the maximum outer diameter D of the first and second meniscus lenses of the distal group is F/D>10.

19 Claims, 3 Drawing Sheets

(58) Field of Classification Search
USPC .......................................................... 359/362
See application file for complete search history.

(56) References Cited

U.S. PATENT DOCUMENTS

| | | | | |
|---|---|---|---|---|
| 2021/0157120 | A1* | 5/2021 | Baumann ........... | A61B 1/00197 |
| 2022/0365315 | A1* | 11/2022 | Nomi ....................... | G02B 9/10 |
| 2023/0055267 | A1* | 2/2023 | Sakurada ................. | A61B 1/05 |

* cited by examiner (state of the art)

ATTACHMENT OPTICS AND SYSTEM FOR FLUORESCENCE IMAGING IN OPEN SURGERY

CROSS-REFERENCE TO RELATED APPLICATION

The present application is based upon and claims the benefit of priority from U.S. Provisional Application No. 63/444,626 filed on Feb. 10, 2023, the entire contents of which is incorporated herein by reference.

BACKGROUND

Field

The present disclosure relates to an attachment optics for a camera head and a system for fluorescence imaging in open surgery.

Prior Art

A medical application of fluorescence imaging, a subtype of molecular imaging, is fluorescent image-guided surgery, a medical imaging technique used to detect fluorescently labelled structures during surgery with the purpose of guiding the surgical procedure and providing the surgeon with real time visualization of the operating field, both in open surgery and in endoscopic procedures. Fluorescent dyes (fluorophores) commonly used in fluorescent image-guided surgery for different applications include indocyanine green (ICG) and others fluorescing in the visible and near infrared spectrum. The visible spectrum is defined by what a typical human eye will perceive, which ranges from about 380 nm to about 750 nm, possible individual deviations from these typical numbers notwithstanding. The boundaries are not sharply defined and may vary with the conditions under which light is perceived.

In the context of the present application, the terms visible spectrum, far red or near infrared are not to be understood as hard boundaries, but to generally conform to the human perception, which does not suddenly stop at 740 nm, but fades out gradually towards longer wavelengths. Likewise, most image sensors' spectral sensitivity distributions have similarly sloped edges.

In terms of fluorescent dyes, or fluorophores, that are used in medical fluorescence imaging, ICG, for example, has an excitation wavelength of between 740 nm and 800 nm and emission wavelength in the range of 800 nm to 860 nm, thereby being at the edge of the visible spectrum in the far red and generally extending into the near infrared spectrum.

One or more light sources are used to excite and illuminate the sample containing the chosen fluorescent dye. Light is collected using optical filters that match the emission spectrum of the chosen fluorescent dye. Imaging lenses and digital cameras having, e.g., CCD, CMOS or InGaAs image sensors are used to produce the final images.

In fluorescence imaging guided surgery, the surgeon gets to view a composite image with an overlay of the fluorescent image over a non-fluorescent background image for easy localization of the fluorescent areas within its surroundings. There are different ways to achieve such an overlay image. One option is that the background image and the overlay image are recorded simultaneously with different video chips and the recorded images are then electronically merged. In this case, the additional chip for the fluorescence is usually sensitive in a wavelength range outside the visible spectrum at wavelengths >700 nm.

Another option is to record a white light image and a fluorescent image alternating with the same video chip by also changing the illumination between white light and excitation light.

If the images may be recorded simultaneously and a camera head with three CCD or CMOS video chips for the blue, green and red channels are used also the blue and green video chips can be used for the white light image and the red video chip can be used for the fluorescent image in the near infrared.

One type of medical imaging systems comprises a camera head with exchangeable optical imaging units that are designed for endoscopic or open surgery applications. A camera head usually comprises one or more optical sensors as well as a cone adapter connecting and securing the ocular cones of optical imaging units to the camera head. Such optical imaging units may be devices for endoscopic procedures, such as rigid telescope type endoscopes having an optical assembly at their distal tip for forming an image of the specified field of view, and one or more relay lens units for relaying the image to the endoscope's ocular for view with the unaided eye, or alternatively, the camera head. For this purpose, the camera head comprises imaging optics that focus on the location of the virtual image projected by the ocular lens of the attached telescopes at their own focal length. This focal length is standardized between different types of telescopes, since they have to be usable with the unaided eye.

For the purpose of capturing the operating area for open surgery, the optical imaging units are often designed to create a virtual image of the operating area with a predefined field of view at a predefined working distance. A typical example is the so-called exoscope, which resembles a short endoscope with an objective lens, a set of relay lens units and an eyepiece. The optical properties of the objective lens are quite different from those of objective lenses of endoscopes because of their very different focal lengths, since, unlike an endoscope, an exoscope is designed to operate outside a human body instead of inside the human body.

In order to illuminate the operating area, the medical imaging systems usually comprise an illumination light generating unit comprising one or more light sources generating the illumination light. The illumination light is transported from the illumination light generating unit to the distal end of an optical imaging unit through a fiber bundle, where it exits the fiber bundle. Although they may have light shaping units such as lenses, endoscopes and exoscopes usually do not comprise any light shaping units at the tip, so that the irradiance distribution at the field of operation is mainly defined by the irradiance distribution with which the light enters the fiber bundle from the light source.

Modern medical imaging systems implement the above-described versatility of endoscopic or open surgery imaging with various telescopes and exoscopes for different applications that can be attached to the system's camera head, which is controlled by a central control unit (CCU). The telescopes and endoscopes may have an illumination light connector to be connected to an illumination light generating unit of the medical imaging system via light fibers. Such systems may furthermore implement fluorescence imaging for fluorescence imaging guided surgery.

Fluorescence imaging is a form of molecular imaging, which generally encompasses imaging methods for visualizing and/or tracking of molecules having specific properties that are used for molecular imaging. Such molecules can be substances that are endogenous to the body, or dyes or contrast agents that are injected into the patient. MRI and CT, for example, therefore, also fall under the term "molecular imaging". Fluorescence imaging as a variant of molecular imaging uses the property of certain molecules (fluorophores), which emit light of certain wavelengths when excited/absorbed by light of certain wavelengths.

For the purpose of fluorescence imaging, the system's camera head includes sensors that are sensitive in the visible spectrum and in the near infrared spectrum, with wavelengths between ca. 400 nm and ca. 1.000 nm, while the system's illumination light generating unit has a light source for white light to illuminate the operating area with white light as well as at least one excitation light source designed to illuminate the operating area with light that includes an excitation wavelength capable of exciting a fluorescent substance or dye that has been injected into the operating area, to return fluorescence emission. The excitation light source may comprise a laser or a light emitting diode, the wavelength depending on the dye used. For indocyanine green (ICG), e.g., which emits fluorescence light between 750 nm and 950 nm, an excitation wavelength may be between 600 nm and 800 nm. After being excited, the dyes shed the excitation energy by emitting light at slightly longer wavelengths than that of the excitation light. Other wavelengths may be used as excitation wavelengths depending on the type of dye used. This can include wavelengths that are further inside the visible spectrum.

While the above-described exoscopes are useful for documenting open surgery, their usefulness for fluorescence imaging in open surgery is limited due to their relatively small distal aperture, limiting the amount of light, in particular the weak fluorescence light, they can take in and transfer to the image sensor or image sensors of the optical system.

SUMMARY

An object is to provide improved means for fluorescence imaging in open surgery.

Such object can be solved by an attachment optics for a camera head for fluorescence imaging in open surgery, with an optical system comprising, in progression from distal to proximal, a distal group of two meniscus lenses, of which one is a negative meniscus and the other a positive meniscus, a biplanar glass rod and single meniscus lens, wherein the two meniscus lenses of the distal group of meniscus lenses are made from different glass types having Abbé numbers $\gamma_1$, $\gamma_2$ with $$|\gamma_1 - \gamma_2| < 20, \text{ such as } |\gamma_1 - \gamma_2| < 5,$$

and refractive indexes $n_1$, $n_2$ with $$0.02 < |n_1 - n_2| < 0.07$$

and wherein the ratio of the focal length F of the optical system to the maximum outer diameter D of the lenses of the distal group of meniscus lenses is F/D>10.

Such an attachment optics can be configured to be attached to a camera head of a medical imaging system. Since the camera head has its own imaging optics, the attachment optics, which can be comparable to a head lens, can be attached to the camera head's cone adapter that provides the combined optical system of the attachment lens system and the camera head's optical imaging system with the focal length and other optical properties necessary for viewing and recording the operating area.

The imaging optics of the camera head can be configured to have its focus at a location where the typically attached endoscopes project a virtual image to be viewed with the naked eye through the eyepiece. The eyepieces of endoscopes are usually adjusted so that the virtual image can be about one meter in front of the eyepiece (−1 diopter). The exit pupil of the endoscopes can be configured to approximately match the entrance pupil of the camera head. By itself, it is not adapted to provide a suitable overview of the operating area in open surgery. The optical system of the attachment optics, or "head lens", decreases the focal length of the combined optical system of head lens and camera head and thereby enlarges its field of view, without introducing noticeable optical aberrations that worsen optical performance, thus rendering it suitable for observing and imaging the operating field. The rather simple combination of a distal group or pair of meniscus lenses, a biplanar glass rod and a proximal meniscus lens provides this longer focus in front of the camera head optics system.

In the attachment optics' optical system, glass types, thicknesses and radii of the surfaces of the meniscus lenses can be chosen appropriately for the desired optical specifications of the system, such as the desired focal length, which can be done by specialists with the aid of dedicated simulation software. With the optical system as described above, the number of variables can be quite manageable.

Still, since the optical system can be used for a wide range in the optical wavelengths to be transmitted, ranging from the visible spectrum to the near infrared, it can be challenging to avoid optical aberrations, such as chromatic aberrations, within the wide wavelength range. Best results are obtained if the Abbé numbers and refractive indices of the glass types used for the two meniscus lenses of the distal group are not too different, as expressed in the above-listed in equations. One of the meniscus lenses of the distal group being a positive meniscus lens, i.e., being thicker at the center than at the edges, and the other one being a negative meniscus lens, i.e., being thinner at the center than at the edges, ensures that chromatic aberrations can be compensated more accurately and finely.

Furthermore, since the attachment optics can be attached to a camera head and to be used to observe an operating field during open surgery from a distance, the optical system can be on the one hand compact, on the other hand to have a larger entrance pupil in order to get higher resolution and brightness. This optimization can be expressed in the inequation relating the focal length F and diameter D of the largest diameter meniscus lens of the distal group.

The two meniscus lenses of the distal group can be kitted together, thereby providing stability and easy assembly.

In embodiments, the two meniscus lenses of the distal group can have identical radii of curvature $R_2$ at their common interfacing surfaces. Having identical radii of curvature at their common interfacing surfaces can have several advantages, including reducing of the number variables in the optimization of the optical properties during development and the ease of assembly, since the two interfacing surfaces fit together perfectly and can be easily kitted, if kitting is performed.

In embodiments, the distal one of the two meniscus lenses of the distal group can have a distal surface with radius of curvature $R_1$, the proximal one of the two meniscus lenses of the distal group can have a proximal surface with radius of curvature $R_3$, wherein one or both of the following conditions (1) and (2) are met:

$$R_1 > R_3 > 0 \text{ and } R_1 > R_2 > 0, \quad (1)$$

$$R_1 > R_3 > R_2 > 0. \quad (2)$$

Keeping these inequations during development and optimization of the optical system, where $R_2$ is, again, the identical radius of curvature of the common interfacing surfaces of the two meniscus lenses of the distal group, can further narrow down the available phase space of optical parameters in a way that ensures that the first meniscus lens of the distal group can be a negative meniscus (thinner in the center) and its second meniscus lens a positive meniscus (thicker in the center), thus ensuring that a proper balance can be reached between diverse optical aberrations. Off-axis aberrations, like astigmatism and lateral chromatic aberration, can be reduced effectively in this configuration.

In a further embodiment, the single meniscus lens proximal of the biplanar glass rod can have a distal surface with radius of curvature $R_4$ and a proximal surface with radius of curvature $R_5$, wherein the following condition (3) is met:

$$R_4 < R_5 < 0. \quad (3)$$

This configuration can ensure that the proximal meniscus lens is a positive meniscus, that proper focusing characteristics are reached and that the incident angle of rays on the surface $R_4$ are reduced in order to reduce the optical aberrations caused by nonlinear effects, e.g., spherical aberration and coma aberration.

The optical system can be integrated into a housing adapted to be attached to a camera head by a releasable fixture mechanism in embodiments. Such releasable fixture mechanism can be a locking or clamping mechanism and can be based on the same configuration and principle as the one used for attaching an endoscope or exoscope to the camera head.

Furthermore, the housing can be equipped with a light source or with a light guide, such as light guiding fibers or one or more solid light guides, configured for illuminating an operating field distal of the housing. Such light guide can provide lighting at a front face of the attachment optics, e.g. in the form of a ring light surrounding the optical system of the attachment optics for even and shadow-free illumination of the operating field.

In further embodiments, the meniscus lens of the distal group situated adjacent to the biplanar glass rod can be attached to the biplanar glass rod by direct gluing or by a mask disk coated with glue on both sides and having a central aperture. The glue can be a transparent optical glue or another glue that may not be transparent. In direct gluing as well as in using a mask disk, glue can only be applied to the circumferential region where there can be direct contact between the opposing surfaces of the meniscus lens and the biplanar rod. In the case of the mask disk as well as if nontransparent glue is used, stray light can be minimized while simultaneously not limiting the overall optical performance of the system.

Similarly, in a further embodiment, the single meniscus lens can be attached to the biplanar glass rod by direct gluing or by a mask disk coated with glue on both sides and having a central aperture. Again, stray light can be eliminated, thereby enhancing the optical performance.

The outer diameter can be chosen such as to cover at least the outer diameter of the adjacent meniscus lens. In order to more effectively eliminate stray lights, the mask disk in embodiments can have an outer diameter equal to between 95% and 100% of an outer diameter of the biplanar glass rod.

In embodiments, a distal one of the two meniscus lenses of the distal group and the biplanar glass rod can have the same diameter or similar diameters that deviate from each other by less than 5%. In embodiments, the single meniscus lens can have a diameter that can be between 60% and 100%, such as between 95% and 100%, of the diameter of the biplanar glass rod. These ranges include their end points. Keeping the same or very similar diameters, the attachment optics can have a basically cylindrical shape from front to back, making it easy to handle and center.

Such object can also be achieved by a system for fluorescence imaging in open surgery, comprising a controller comprising hardware, a camera head connected to and controlled by the controller and an above-described attachment optics for fluorescence imaging in open surgery, the camera head and the attachment optics being attached to one another. The system thereby incorporates all features, advantages and characteristics of the above-described attachment optics.

In embodiments of the system, at least one of the controller, the camera head, the attachment optics and a separate lighting unit can be configured to produce illumination light for fluorescence imaging, such as to be emitted by the attachment optics. Such lighting can include both white illumination lighting and fluorescence excitation lighting for a predetermined selection of fluorescent dyes to be used during fluorescence imaging guided endoscopic and/or open surgery. Fluorescence excitation lighting can be generated by narrow band light sources such as LEDs or appropriately configured or tuned lasers in the far red or near infrared range, but also in the visible spectrum for fluorophores that are excited and emit fluorescence light in the visible spectrum.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general intent of the invention, based on exemplary embodiments, wherein reference is made expressly to the drawings with regard to the disclosure of all details that are not explained in greater detail in the text.

In the drawings:

Figure 1:
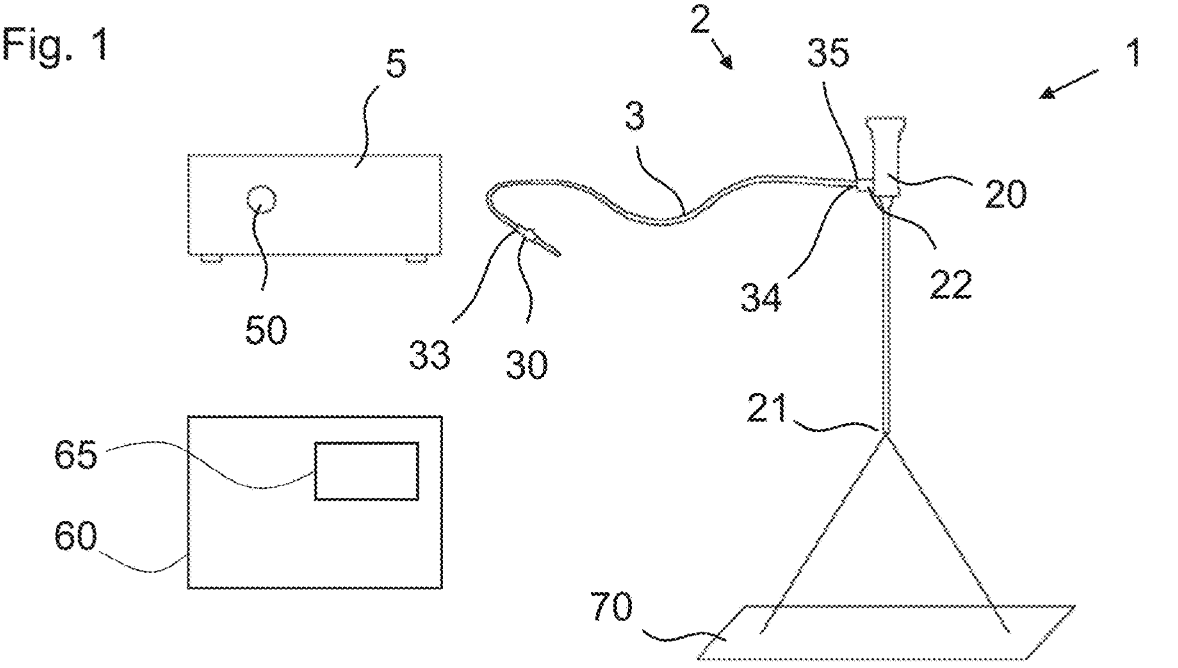
Figure 2:
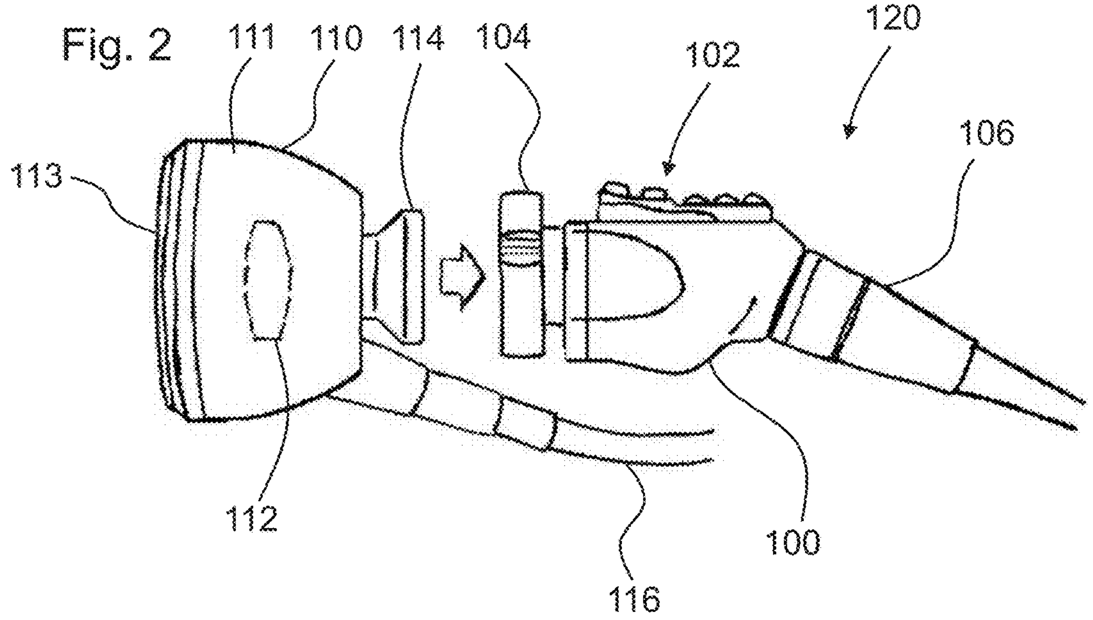
Figure 3A:
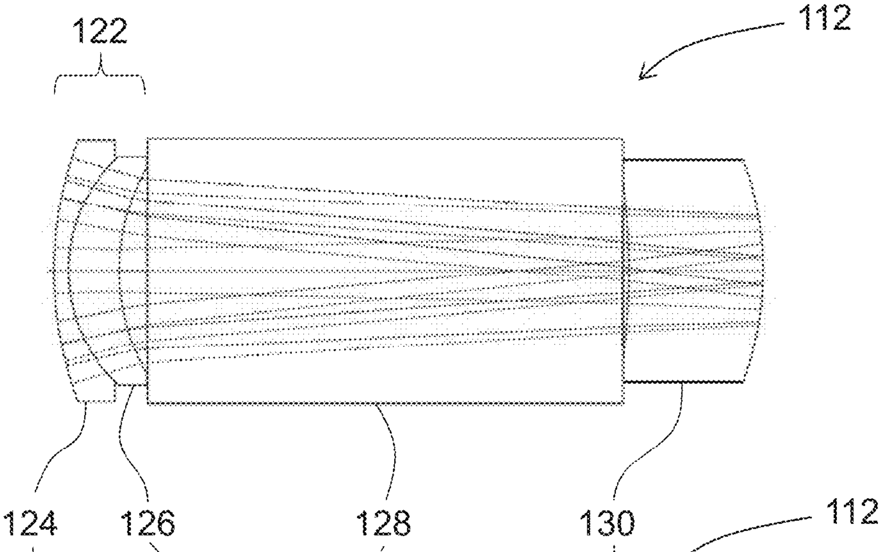
Figure 3B:
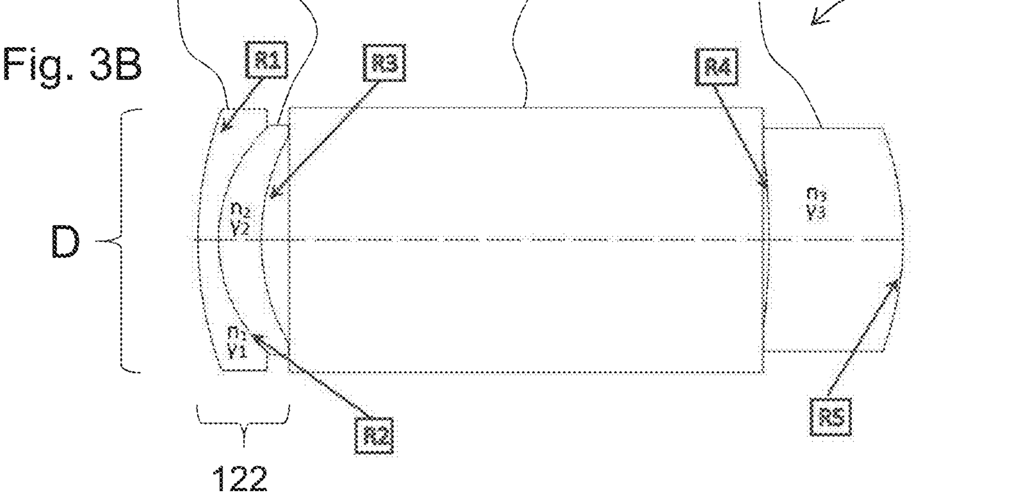
Figure 4A:
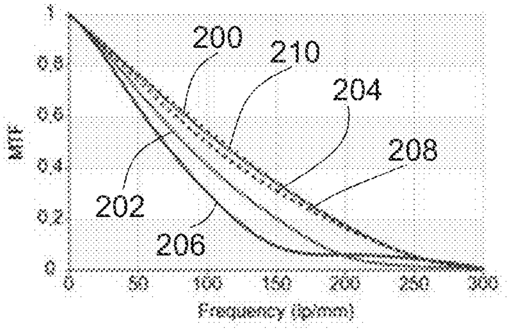
Figure 4B:
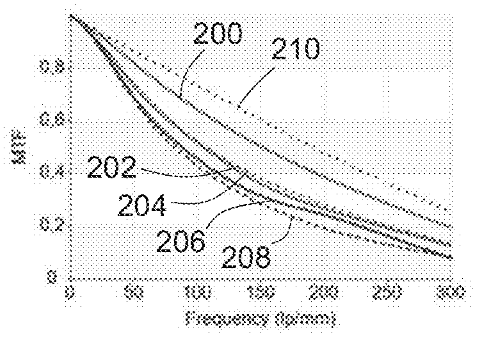
Figure 5:
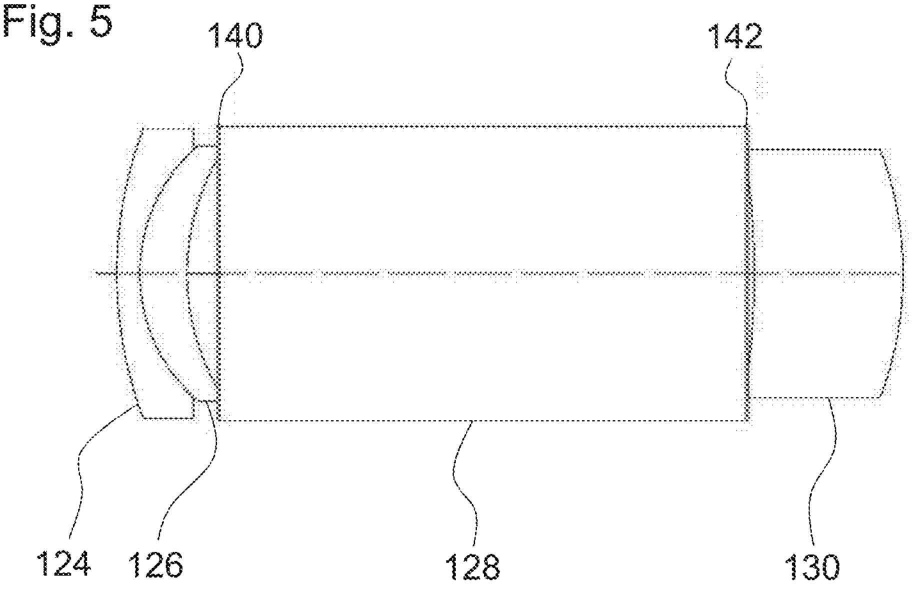
Figure 6:
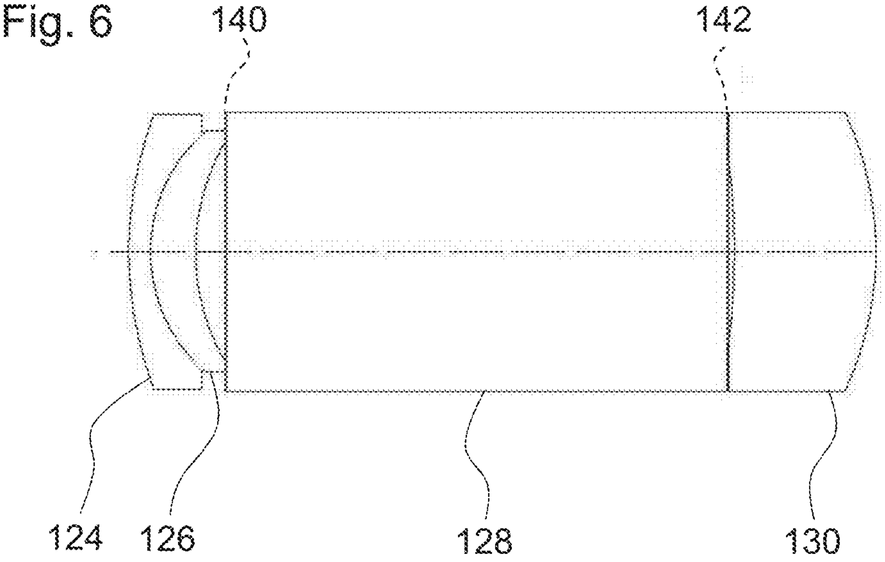

FIG. 1 illustrates a schematic simplified representation of an exoscope system comprising a light source and an exoscope with a light guide cable, FIG. 2 illustrates a schematic simplified representation of a camera head with attachment optics, FIG. 3A illustrates optical elements of an optical system of an attachment optics according to an embodiment, FIG. 3B illustrates the optical elements of FIG. 3A with added nomenclature, FIG. 4A illustrates a representation of a matrix transfer function of an exoscope optics, FIG. 4B illustrates a representation of a matrix transfer function of an optical system of an embodiment of an attachment optics, FIG. 5 illustrates optical elements of another embodiment of an attachment optics and FIG. 6 illustrates optical elements of another embodiment of an attachment optics.

In the drawings, the same or similar types of elements or respectively corresponding parts are provided with the same reference numbers in order to prevent the item from needing to be reintroduced.

DETAILED DESCRIPTION

FIG. 1 shows a schematically simplified representation of an exoscope system 1 commonly used for open surgery. The exoscope system 1 comprises an illumination light source unit 5 and an exoscope 2 with a light guide cable 3. The light guide cable 3 may be part of the exoscope 2 or separate to the exoscope 2. The exoscope 2 is configured to image an operating area 70 with an optical imaging unit not shown in FIG. 1.

In order to illuminate the operating area 70 when observing it, the exoscope 2 further comprises illumination optics configured to guide light from the illumination light source unit 5 to an exoscope tip 21 of the exoscope 2. To this end, the light source unit 5, which is further described with reference to FIG. 3, comprises a light source port 50 configured to receive a light source connector 30 arranged at a first end 33 of the light guide cable 3. The second end 34 of the light guide cable 3 is connected to an exoscope body 20 of the exoscope 2. This is done with an exoscope connector 35 of the light guide cable 3 and a light guide cable connector 22 of the exoscope body 20. With these connectors 22, 35, the light guide cable 3 is detachable from the exoscope body 20. Inside the light guide cable 3 and the exoscope body 20, fiber bundles guide illumination light to the distal tip 21 of the exoscope 20. However, as the illumination light exits the fiber bundle at the exoscope tip 21, an irradiance distribution of the light is usually too broad for the observed operating area 70. Thus, only a part of the emitted light actually illuminates the operating area 70. This is undesired, because it lowers the light intensity inside the operating area 70.

FIG. 1 also schematically displays a controller comprising hardware 60 set up to control the operation of the exoscope 2. Controller 60 can be configured as dedicated hardware circuits or a hardware processor executing a series of software instructions. The controller 60 can be set up to receive video signals from the exoscope 2, which may either be connected to a camera head connected to the exoscope, e.g., such as the one shown in FIG. 2, or have its own image sensor or sensors. The video signals are processed in an image processor 65, which may be a subunit of controller 60, integral with the controller 60, or be external to and separate from the controller 60. Image processor 65 can be configured as dedicated hardware circuits or a hardware processor executing a series of software instructions.

FIG. 2 illustrates a schematic representation of a medical imaging device in the form of a combination of a camera head 100 and a fluorescence imaging adapter configured as attachment optics 110 as part of an exemplary embodiment of a medical fluorescence imaging system 120. The camera head 100 is configured for white light imaging as well as fluorescence imaging. It is handheld and has control buttons 102 on the top of its housing, an adapter 104 for attachment of various optics systems at its front surface and a connecting cable 106 for power and signal transmission leading to a central controller such as the one shown in FIG. 1.

Since the camera head 100 is configured to receive telescope type endoscopes with eyepieces (ocular cones), its adapter 104 may be configured to receive such eyepieces. The imaging optics is configured to have its focus at a location where the typically attached endoscopes project a virtual image to be viewed with the naked eye through the eyepiece. The eyepieces of endoscopes are usually adjusted so that the virtual image is about one meter in front of the eyepiece (−1 diopter). The exit pupil of the endoscopes is configured to approximately match the entrance pupil of the camera head and is located about 7 mm behind the edge of the eyepiece funnel, which is typically inside adapter 104 in the attached state.

The fluorescence imaging adapter 110 provides a head lens or attachment lens in the form of a head lens system 112 having one or more individual lenses whose function it is to change the properties of the imaging optics of camera head 100, thus rendering the camera head 100 capable of viewing the operating field. This is be done, e.g., by decreasing the focal length of the camera head 100 and thereby enlarging its field of view. The fluorescence imaging adapter has a standardized ocular cone 114 on its rear side for the purpose of connecting to the adapter 104 of camera head 100. Furthermore, the fluorescence imaging adapter 110 is equipped with a light guide cable 116 leading towards its front surface 113. The other end of the light guide cable 116 may be connected to an illumination light source unit 5 as shown in FIG. 1.

FIG. 3A shows an assembly of optical components of an embodiment of an optical system 112 of attachment optics 110 comprising, from most distal to most proximal, a distal group 122 of meniscus lenses including a first meniscus lens 124 and a second meniscus lens 126, a biplanar glass rod 128 and a single meniscus lens 130. The first and second meniscus lenses 124, 126 of the distal group 122 are a negative meniscus lens 124 having a center thinner than its edges and a positive meniscus lens 126 having a center thicker than its edges. The radii of curvature of the interfacing surfaces of meniscus lenses 124 and 126 is equal to each other. The proximal single meniscus lens 130 is thicker in its center than at its edges. Furthermore, FIG. 3A shows light ray paths of light rays that enter the optical system 112 centrally and peripherally, the peripheral ones entering under different angles, denoting extreme cases.

FIG. 3B displays the nomenclature used within the context of the present application. The first meniscus lens 124 of distal group 122 is made from a material having Abbé number 71 and refractive index $n_1$. The radius of curvatures of its distal and proximal surfaces are $R_1$ and $R_2$. Likewise, the second meniscus lens 124 of distal group 122 is made from a, usually different, material having Abbé number $\gamma_2$ and refractive index $n_2$. The radii of curvature of its distal and proximal surfaces are $R_2$, which is equal to the radius of curvature of the proximal surface of first meniscus lens 124, and $R_3$. The first and second meniscus lenses 124, 126 of the distal group 122 may be kitted together with optical kit at their common interface. Finally, the proximal single meniscus lens 130 is made from a material having Abbé number $\gamma_3$ and refractive index $n_3$. The radii of curvature of its distal and proximal surfaces are $R_4$ and $R_5$, respectively.

First Exemplary Embodiment

A first exemplary embodiment having a focal length F of 762 mm is shown in the following Table 1 (all units in mm):

TABLE 1

| Surface | Radius | Thickness | Glass | D |
|---|---|---|---|---|
| Object | | 200 | | |
| 1 | $R_1 = 23.1$ | 1.3 | $n_1 = 1.804, \gamma_1 = 39.6$ | 16 |
| 2 | $R_2 = 9.56$ | 2.68 | $n_2 = 1.762, \gamma_2 = 40.1$ | 14 |
| 3 | $R_3 = 13.04$ | 1.77 | | 13 |
| 4 | ∞ | 29.85 | $n = 1.923, \gamma = 18.9$ | 16 |
| 5 | ∞ | 0.38 | | 16 |
| 6 | $R_4 = -42.79$ | 8.44 | $n_3 = 1.516, \gamma_3 = 64.1$ | 11 |
| 7 | $R_5 = -19.61$ | 1 | | 11 |

In Table 1, each line represents a specific location, starting with an object "Object", such as an operating field 70. At a distance ("Thickness") of 200 mm behind this object the distal surface ("1") of the distal meniscus lens 124 of FIGS. 3A, 3B is listed with its radius of curvature, lens thickness, glass properties and lens diameter D. The next line ("2") represents the proximal surface of first meniscus lens 124 as well as the distal surface of second meniscus lens 126, since their radii of curvature is identical. Line "2" lists the corresponding thickness, glass properties and diameter of second meniscus lens 126, followed in line "3" by an air space with 1.77 mm thickness, which is started by the proximal surface of meniscus lens 126, whose radius of curvature $R_3$ is given in line "3". The next two lines "4" and "5" correspond to the distal and proximal planar surfaces of biplanar glass rod 128, the radius is infinite in both cases. The air space proximal to the glass rod 128 has a thickness of 0.38 mm.

Lines "6" and "7" denote the distal and proximal surfaces of the single proximal meniscus lens 130.

This optical system is followed by a camera head, whose optical characteristics are not given in Table 1 but are known when calculating and optimizing attachment optics for a specific camera head.

Second Exemplary Embodiment

A second exemplary embodiment having a focal length F of 205 mm is shown in the following Table 2 (all units in mm):

TABLE 2

| Surface | Radius | Thickness | Glass | D |
|---|---|---|---|---|
| Object | | 200 | | |
| 1 | $R_1 = 15.34$ | 1 | $n_1 = 1.804, \gamma_1 = 39.6$ | 14 |
| 2 | $R_2 = 7.02$ | 1.5 | $n_2 = 1.757, \gamma_2 = 47.8$ | 12 |
| 3 | $R_3 = 7.43$ | 2 | | 14 |
| 4 | ∞ | 22.41 | $n = 1.959, \gamma = 17.5$ | 14 |
| 5 | ∞ | 0.54 | | 14 |
| 6 | $R_4 = -28.23$ | 2.19 | $n_3 = 1.517, \gamma_3 = 71.8$ | 11 |
| 7 | $R_5 = -10.72$ | 1 | | 11 |

This optical system, calculated for a different camera head having a slightly longer focal length, is more compact than the first exemplary embodiment, both in length and in diameter.

FIGS. 4A and 4B show the modulation transfer functions (MTF) of a known exoscope (FIG. 4A) and of an optical system 112 of an attachment optics according to the present application, calculated over the entire spectrum of a light source. The MTF describes the optical system in terms of contrast at different spatial frequencies, expressed in line pairs per mm (lp/mm). Higher spatial frequencies correspond to finer details. An MTF value of 1 means perfect contrast, 0 is no contrast at all, white and black lines cannot be distinguished anymore at all.

Generally the solid lines represent MTF in the tangential direction, the dashed lines represent MTF in the sagittal direction. MTF 210 represented by a dotted line represents the theoretical ideal case of a diffraction-limited system. As can be seen in FIG. 4A, even the theoretical optimum involves the MTF decreasing rapidly towards finer details.

Line 200 denotes the MTF in the center of the image plane, which is the same in the sagittal and tangential directions, and is very close to the theoretical optimum. Lines 202 and 204 denote the MTF at 80% image size in the tangential and sagittal directions, respectively, lines 206 and 208 the MTF at 100% image size, i.e., at the far edge. As can be seen, the MTF stays close to the ideal values in the sagittal direction, whereas it is significantly worse in the tangential direction in both cases.

In the case of the optical system 112 of the attachment optics, shown in FIG. 4B, the values are markedly better, owing in part to the fact that the different optical setup increases the MTF 210 in the theoretical ideal, diffraction limited system. Although even the MTF 200 in the center of the image plane (central ray) does not reach the theoretical optimum, the MTFs are overall significantly improved, especially at high spatial frequencies, leading to clearer and more detailed images. Furthermore, at 80% image size as well as at 100% image size, in each case the MTFs 202 and 204, and 206 and 208, respectively, are much closer to each other than in the case of FIG. 4A. Consequently, image quality does not depend as much on the orientation of the fine details inside the picture, which can be important for some features, such as thin blood vessels.

FIG. 5 illustrates optical elements of another embodiment of an attachment optics similar to that of FIGS. 3A and 3B. In addition, the biplanar glass rod 128 is connected on its two planar end faces with the adjacent meniscus lenses 126, 130 by mask disks 140, 142, respectively. The mask disks 140, 142 have annular or ring shapes covering at least area in which the meniscus lenses 126, 130 make contact with the planar end faces of biplanar glass rod 128, respectively, and may have an outer diameter such as to coincide with the outer diameter of biplanar glass rod 128. Their central apertures allow all the light of the optical light path defined by the optical elements to pass, whereas stray light is eliminated, thus enhancing the optical performance of the system.

FIG. 6 illustrates optical elements of another embodiment of an attachment optics, which differs from the previous embodiments in that diameter of the proximal single meniscus lens 130 is equal or close to the diameter of biplanar glass rod 128. The diameter of the distal meniscus lens 124 has the same or very similar diameter, providing the whole optical assembly with a basically uniform outer diameter, making it easy to handle. There may be one or more of mask disks 140 and 142 for eliminating stray light as well.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

1 medical multi-dye fluorescence imaging system
2 exoscope
3 light guide cable
5 light source unit
20 exoscope body
21 exoscope tip
22 light guide cable connector
30 light source connector
33 first end
34 second end
35 medical imaging device connector
50 light source port
51 white illumination light source
52, 53 first fluorescence excitation light source
54 second fluorescence excitation light source
56 light guide
60 controller
62 image processor
70 operating area
100 camera head
102 control buttons
104 adapter for attachment devices
106 connecting cable
110 attachment optics
111 housing
112 optical system
113 front surface
114 ocular cone
116 light guide cable
120 medical fluorescence imaging system
122 distal group
124 first meniscus lens
126 second meniscus lens
128 biplanar glass rod
130 single meniscus lens
140 mask disk
142 mask disk
200 MTF in center of image plane
202 MTF at 80% image size, tangential
204 MTF at 80% image size, sagittal
206 MTF at 100% image size, tangential
208 MTF at 100% image size, sagittal
210 MTF for diffraction-limited system

What is claimed is:

1. Attachment optics for use with a camera head for fluorescence imaging in open surgery, the attachment optics comprising:

an optical system comprising, in progression from distal to proximal:

a distal group of first and second meniscus lenses, the first meniscus lens being a negative meniscus lens and the second meniscus lens being a positive meniscus lens, a bi planar glass rod; and a third meniscus lens;

wherein the first meniscus lens of the distal group is made from a first glass material having Abbe number $_{y1}$ and the second meniscus lens of the distal group is made from a second glass material having Abbé number $_{y2}$, different from Abbé number $_{y1}$, with $$|y1 - y2| < 20,$$

and the first and second meniscus lenses having refractive indexes $_{n1}$, $_{n2}$, respectively, with $$0.02 < |n_1 - n_2| < 0.07$$

and wherein the ratio of a focal length F of the optical system to the maximum outer diameter D of the first and second meniscus lenses of the distal group is F/D >10.

2. The attachment optics according to claim 1, wherein $$|y1 - y2| < 5.$$

3. The attachment optics according to claim 1, wherein the first and second meniscus lenses of the distal group are kitted together.

4. The attachment optics according to claim 1, wherein the first and second meniscus lenses of the distal group have identical radii of curvature $_{R2}$ at common interfacing surfaces.

5. The attachment optics according to claim 4, wherein a distal one of the first and second meniscus lenses of the distal group has a distal surface with a radius of curvature $_{R1}$, a proximal one of the first and second meniscus lenses of the distal group has a proximal surface with a radius of curvature $_{R3}$, wherein one or both of the following conditions (1) and (2) are met:

$$R1 > R3 > 0 \text{ and } R1 > R2 > 0, \quad (1)$$

$$R1 > R3 > R2 > 0. \quad (2)$$

6. The attachment optics according to claim 4, wherein the third meniscus lens proximal of the bi planar glass rod has a distal surface with a radius of $_{R5}$ curvature $_{R4}$ and a proximal surface with a radius of curvature $_{R5}$, wherein the following condition (3) is met:

$$R4 > R5 > 0. \quad (3)$$

7. The attachment optics according to claim 1, wherein the optical system is integrated into a housing adapted to be attached to a camera head by a releasable fixture mechanism.

8. The attachment optics according to claim 7, wherein the housing having one of a light source, or a light guide, configured for illuminating an operating field distal of the housing.

9. The attachment optics according to claim 8, wherein the light guide comprises light guiding fibers.

10. The attachment optics according to claim 8, wherein the light guide comprises one or more solid light guides.

11. The attachment optics according to claim 1, wherein one of the first or second meniscus lenses of the distal group situated adjacent to the bi planar glass rod is attached to the biplanar glass rod by one of direct gluing or by a mask disk coated with glue on both sides and having a central aperture.

12. The attachment optics according to claim 1, wherein the third meniscus lens is attached to the biplanar glass rod by one of direct gluing or by a mask disk coated with glue on both sides and having a central aperture.

13. The attachment optics according to claim 11, wherein the mask disk has an outer diameter equal to between 95% and 100% of an outer diameter of the biplanar glass rod.

14. The attachment optics according to claim 12, wherein the mask disk has an outer diameter equal to between 95% and 100% of an outer diameter of the biplanar glass rod.

15. The attachment optics according to claim 1, wherein one of:

a distal one of the first and second meniscus lenses of the distal group and the biplanar glass rod have the same diameter or similar diameters that deviate from each other by less than 5%, and the third meniscus lens has a diameter that is between 60% and 100% of the diameter of the bi planar glass rod.

16. The attachment optics according to claim 15, wherein the third meniscus lens has a diameter that is between 95% and 100% of the diameter of the biplanar glass rod.

17. A system for fluorescence imaging in open surgery, the system comprising:

a controller comprising hardware, a camera head connected to and controlled by the controller; and the attachment optics according to claim 1, wherein the camera head and the attachment optics being attached to each other.

18. The system according to claim 17, wherein at least one of the controller, the camera head, the attachment optics and a separate lighting unit is configured to produce illumination light for fluorescence imaging.

19. The system according to claim 17, wherein the illumination light for fluorescence imaging is emitted by the attachment optics.

* * * * *